United States Patent [19]

Kingston et al.

[11] Patent Number: 5,137,805
[45] Date of Patent: Aug. 11, 1992

[54] METHOD OF DIAGNOSING STRESS CONDITION BY SPECIFIC BINDING OF HUMAN HEAT SHOCK FACTOR

[75] Inventors: Robert E. Kingston, Brighton; Thomas J. Schuetz, Jamaica Plain, both of Mass.

[73] Assignee: The General Hospital Corporation, Boston, Mass.

[21] Appl. No.: 301,417

[22] Filed: Jan. 25, 1989

Related U.S. Application Data

[63] Continuation-in-part of Ser. No. 169,965, Mar. 18, 1988, abandoned.

[51] Int. Cl.$^5$ ............................ C12Q 1/68; G01N 33/53
[52] U.S. Cl. .................................. 435/6; 435/7.1; 435/7.9; 436/501; 436/518; 436/536; 436/811; 436/815
[58] Field of Search ............... 435/7, 29, 810, 261, 435/6, 7.1, 7.9; 436/811, 815, 501, 518, 536

[56] References Cited

U.S. PATENT DOCUMENTS

| | | | |
|---|---|---|---|
| 4,444,744 | 4/1984 | Goldenberg | 424/1.1 |
| 4,603,106 | 7/1986 | Cerami et al. | 435/29 |
| 4,701,406 | 10/1987 | Chou . | |

OTHER PUBLICATIONS

R. E. Kingston et al., *Mol Cell Biol.*, vol. 7, No. 4, pp. 1530–1534, Apr. 1987.
P. K. Sorger et al., *Nature*, vol. 329, pp. 81–84, 1987.
J. D. Dignam et al., *Nucl Acids Res.*, vol. 11, No. 5, pp. 1475–1489, 1983.
G. Wiederrecht et al., *Cell*, vol. 48, pp. 507–515 (1987).
Dorlando Medical Dictionary, W. B. Saunders Co., 24th Ed., p. 79 (1989).
Schlesinger et al., Heat Shock from Bacteria to Man, Cold Spring Harbor Laboratory, pp. 1, 5, 3, 192, 376 (1982).
G. Herrick, *Nucleic Acids Research*, 8, (16) 3721–3728 (1980).
H. Bünemann et al., *Nucleic Acids Research*, 5, (3) Mar. 1978, pp. 1059–1074.
D. K. R. Low, *J. Chem. Tech. Biotechnol.* 36: 345–350 (1986).
Lindquist, S., *Ann. Rev. Biochem.* 55:1151–91 (1986).
Wu, C., *Nature* 286:854–860 (1980).
Wu, C., *Nature* 309:229–234 (1984).
Wu, C. *Nature* 317:84–87 (1985).
Zimarino, V. et al., *Nature* 327:727–730 (1987).
Craig, E. A., *CRC Crit. Rev. Biochem.* 18:239–279 (1985).
Pelham, H., *Trends in Genetics* 1:31–35 (1985).
Mirault, M. E. et al., *EMBO J.* 1:1279–1285 (1982).
Wu, B. et al., *Mol. and Cell. Biol.* 5:330–340 (1985).
Voellmy, R. et al., *Proc. Natl. Acad. Sci. USA* 82:4949–4953 (1985).
Drabent, B. et al., *Nucl. Acids Res.* 14:8933–8948 (1986).
Morgan, W. D. et al., *Mol. and Cell. Biol.* 7:1129–1138 (1987).
Wu, C., et al. *Science* 238:1247–1253 (1987).

*Primary Examiner*—Esther L. Kepplinger
*Assistant Examiner*—Toni R. Scheiner
*Attorney, Agent, or Firm*—Sterne, Kessler, Goldstein & Fox

[57] ABSTRACT

The present invention relates to Heat Shock Factor, and its derivatives, antagonists, and agonists. The invention also pertains to the production and purification of such compounds from natural and recombinant sources. The invention additionally pertains to diagnostic and therapeutic applications for such compounds.

14 Claims, 1 Drawing Sheet

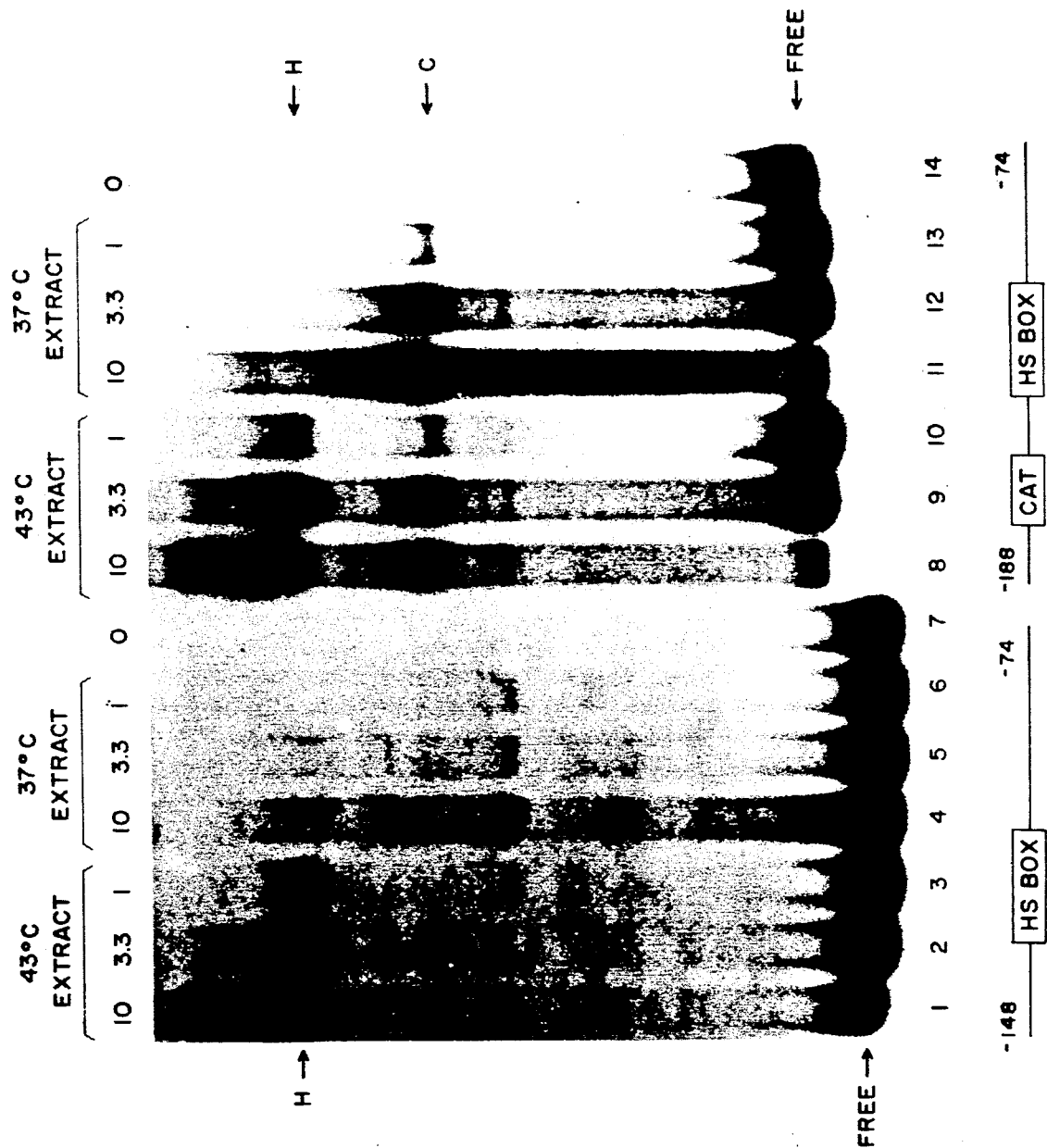

METHOD OF DIAGNOSING STRESS CONDITION BY SPECIFIC BINDING OF HUMAN HEAT SHOCK FACTOR

CROSS-REFERENCE TO RELATED APPLICATIONS

This application is a continuation-in-part of U.S. patent application Ser. No. 169,965 filed Mar. 18, 1988, now abandoned.

FIELD OF THE INVENTION

The present invention relates to a human heat shock factor, and to the use of this factor in the diagnosis and treatment of disease and stress. The invention also pertains to the production of this factor by recombinant DNA techniques, and to DNA sequences which encode this factor.

BACKGROUND OF THE INVENTION

Cells exposed to elevated temperatures or certain chemical agents respond to such stress by inducing the synthesis of a small set of proteins. This cellular response is termed a "heat shock response." The proteins synthesized in response to stress are termed "heat shock proteins" or "HSP." The heat shock response is believed to be ubiquitous, and has been observed in prokaryotic as well as eukaryotic cells and organisms (including man). The synthesis of the heat shock proteins is highly significant since failure to produce these proteins in response to stress is associated with cell death and with tissue and organ injury. The heat shock proteins are believed to play a role in attenuating the severity of the stress, and, in thereby returning the affected cell to a quiescent state. Excellent reviews of the heat shock phenomenon are provided by Lanks, K. W. (*Exper. Cell Res.* 165:1-10 (1986)) and Lindquist, S. (*Ann. Rev. Biochem.* 55:1151-1191 (1986)), which references are hereby incorporated by reference.

The heat shock proteins have been found to possess functions which are unrelated to, and independent of, their role in the heat shock phenomenon. The genes which encode the heat shock proteins (i.e. hsp genes) have been found to be differentially expressed during embryonic development (Bensaude, O. et al., *Nature* 305:331 (1983)), during differentiation of specific cell types such as myoblasts, embryonal carcinoma, and erythroid cells (Atkinson, B. G., *J. Cell. Biol.* 89:666 (1986); Atkinson, B. G. et al., *Can. J. Biochem. Cell. Biol.* 61:404 (1983); Morange, M. et al., *Molec. Cell. Biol.* 4:730 (1984); Singh, M. K. et al., *Nature* 309:631 (1984)). Neoplastic transformation is also associated with a change in the level of the heat shock proteins (Lanks, K. W., *Exper. Cell Res.* 165:1-10 (1986)).

The genes for the heat shock proteins have been found to possess highly conserved 5' sequences which contain a rotationally symmetric consensus sequence known as the "Heat Shock Element" or "HSE". A heat shock transcriptional factor ("HSTF" or "HSF") has been identified which is believed to bind to the HSE sequences, and to play a role in the transcription of the genes which encode the heat shock proteins (Lindquist, S. (*Ann. Rev. Biochem.* 55:1151-1191 (1986); Parker, C. S. et al., *Cell* 36:357-369 (1984); Parker, C. S. et al., *Cell* 37:253-262 (1984); Wu, C., *Nature* 286:854-860 (1980); Wu, C., *Nature* 309:229-241 (1984); Wu, C., *Nature* 317:84-87 (1985)). As such, this factor is capable of regulating and augmenting the heat shock response of an individual.

Thus, this factor, and agents which promote the activity of this factor, provide a therapy for diseases which are associated with the heat shock response. Because this factor has not been sufficiently characterized to permit its use in the therapy for such diseases, or the permit the identification of agents which promote its activity, it has not previously been possible to employ HSF (or such agents) as the basis for a treatment of such diseases. Thus, a need exists for a means for purifying and producing HSF and its derivatives, antagonists, and agonists.

SUMMARY OF THE INVENTION

The present invention relates to Heat Shock Factor, and its derivatives, antagonists, and agonists. The invention also pertains to the production and purification of such compounds from natural and recombinant sources. The invention additionally pertains to diagnostic and therapeutic applications for such compounds.

In detail, the invention concerns a compound comprising Heat Shock Factor substantially free of natural contaminants, or derivatives thereof.

The invention further includes a therapeutic medicament comprising Heat Shock Factor or an agent which activates Heat Shock Factor.

The invention also includes a recombinant nucleic acid molecule comprising a sequence which encodes Heat Shock Factor.

The invention also pertains to the above compound, wherein the compound is prepared by a process comprising DNA affinity chromatography.

The invention also pertains to a method for purifying Heat Shock Factor which comprises subjecting a sample suspected of containing the factor to DNA affinity chromatography.

The invention further provides a method for treating a disease associated with the heat shock response which comprises providing to an individual in need of such treatment an effective amount of activated heat shock factor or an agent which activates heat shock factor.

The invention additionally pertains to a method for diagnosing the stress condition of a patient which comprises assaying for the presence of activated heat shock factor.

BRIEF DESCRIPTION OF THE DRAWINGS

FIG. 1 shows the mobility of human heat shock factor on a non-denaturing polyacrylamide gel. DESCRIPTION OF THE PREFERRED EMBODIMENTS

The Heat Shock Response

The present invention derives, in part, from studies of the response of human cells to changes in the external environment. Human cells respond to a variety of environmental changes by coordinately inducing an appropriate set of genes, frequently via the sequence-specific binding of a transcription factor to regulatory promoter sites (Serfling, E. et al., *Trends in Genet.* 1:224 (1985); McKnight, S. et al., *Cell* 46:795 (1986); Maniatis, T. et al., *Science* 236:1237 (1987)). In several instances, coordinate regulation of mammalian genes appears to involve modification of a pre-existing transcription factor to a form that can bind the regulatory element of a promoter (Yamamoto, K. *Ann. Rev. Genet.* 19:209 (1985); Sen, R. et al., *Cell* 47:921 (1986); Prywes, R. et al., *Cell* 47:777 (1986); Hayes, T. E. et al., *Proc. Natl. Acad. Sci. USA* 84:1272 (1987); Kingston R. E. et al., *Mol. Cell. Biol.* 7:1530 (1987); Zimarino, V. et al., *Nature* 327:727 (1987). Little is known about the biochemical changes that cause this alteration of DNA-binding capability. These changes are clearly an essential link in the transduction of an environmental signal to an appropriate response: induction of a specific set of genes. Determining the mechanism by which transcription factor binding can be induced is therefore essential to understanding many regulatory pathways.

Environmental signals lead to post-translational changes in the DNA-binding ability of several factors that regulate mammalian transcription. In prokaryotic systems, environmental signals can lead to phosphorylation of DNA-binding regulatory proteins: for example, the ntrB product phosphorylates the NtrC protein in response to nitrogen limitation, resulting in activation of NtrC. Similarly, yeast HSF becomes phosphorylated in response to heat.

As discussed above, the heat shock response, which occurs in organisms from bacteria to humans involves the enhanced synthesis of a set of protective proteins encoded by the hsp genes. The transcription of these genes is regulated by "heat shock factor" ("HSF"). HSF is normally produced at a low level, even in quiescent cells. In response to stress, however, the HSF concentration in a cell increases, and is converted into an activated form. The activated form of HSF is capable of binding to the HSE sequences, and of thereby mediating the enhancement of the transcription of the heat shock protein-encoding genes. Thus, the heat shock response is an example of coordinated gene regulation.

When human cells are heated to 43° C., transcription of the heat shock genes has been found to be induced (Ritossa, F. M., *Experientia (Basel)* 18:571 (1962): Nover. L., *Heat Shock of Eukaryotic Cells.* Springer, Berlin (1984); Craig, E. A., *CRC Cit. Rev. Biochem.* 18:239 (1985); Pelham, H. R. B., *Trends Genet.* 1:31 (1985); Lindquist, S., *Ann. Rev. Biochem.* 55:1151 (1986)) through the palindromic heat shock element s(HSEs) located upstream of each promoter (Pelham, H. R. B. et al., *EMBO J.,* 1:1473 (1982); Mirault, M. E. et al., *EMBO J.* 1:1279 (1982): Wu, B. et al., *Mol. Cell. Biol.* 5:330 (1985); Voellmy et al., *Proc. Natl. Acad. Sci. USA* 82:4949 (1985); Drabent B. et al., *Nucl. Acids Res.* 14:8933 (1986): Berger, E. M. et al., *Somat. Cell. Molec. Genet.* 12:433 (1986); Wu. B. J. et al., *Proc. Natl. Acad. Sci. USA* 83:629 (1986)).

Binding of HSF to the HSE has been found to directly stimulate transcription in Drosophila, and is believed to similarly stimulate expression of heat shock genes in other organisms (Kingston R. E. et al., *Mol. Cell. Biol.* 7:1530 (1987); Wu, C., *Nature* 309:229 (1984); Parker, C. S. et al., *Cell.* 37:273 (1984); Morgan, W. D. et al., *Mol. Cell. Biol.* 7:1129 (1987): Wiederrecht, G. et al., *Mol. Cell. Biol.* 7:1129 (1987): Wiederrecht, G. et al., *Cell* 48:507 (1987); Wu et al., *Science* 238 1249 (1987); Sorger, P. K. et al., *Nature* 329:81 (1987)). The ability of HSF to bind the HSE is heat-inducible, by a post-translational mechanism, in Drosophila and human cells (Kingston R. E. et al., *Mol. Cell. Biol.* 7:1530 (1987); Zimarino, V. et al., *Nature* 327:727 (1987); Sorger, P. K. et al., *Nature* 329:81 (1987)).

Induction of the ability of a factor to bind to the HSE of heat shock genes is apparently central to control of the heat shock response in Drosophila and human cells.

The induction of binding ability occurs as a direct response to temperature, as binding is induced in the cytoplasmic extract with approximately the same temperature profile as in an intact cell. This change in binding ability is not the only alteration of HSF that occurs when cells are heated. HSF from heated cells is apparently phosphorylated to a significantly greater degree than HSF activated in vitro. HSF is activated in human cells by at least two steps: an induction of binding ability followed by phosphorylation. Heating a cytoplasmic extract recreates only the first of these steps, resulting in a factor with lower apparent molecular weight. This putative phosphorylation event may increase the ability of HSF to activate transcription, or may alter some other characteristic critical to HSF function.

Thus, in summary, HSF is a transcriptional factor which, when activated by a cell's exposure to heat or stress, mediates the enhanced transcription of the hsp genes, and thereby causes an increase in the cellular concentration of heat shock proteins. The heat shock proteins act to attenuate the harmful effects of the stress.

The Purification of HSF

Activated HSF is preferably purified from HeLa cells, however, other human cells may be employed for this purpose. The cells are cultured in a suitable culture medium, preferably Minimal Essential Medium (Joklik's Modification) supplemented with serum. After the cells have reached a desirable density, they are harvested and used to prepare nuclear extracts. Such extracts are preferably prepared according to the method of Dignam, D. et al., (*Nucl. Acids Res* 11:1475 (1983)).

The nuclear extract is then passed through a double stranded DNA-cellulose column. Bound material is eluted from the column using a step elution with 0.3M KCl. HSF activity is preferably assayed using the gel electrophoresis assay of Kingston, R. E. et al. (*Molec. Cell. Biol.* 7:1530 (1987) which reference is herein incorporated by reference). Fractions containing HSF activity are pooled, in preparation for further purification.

A double-stranded DNA affinity column is prepared which preferably uses a concatemer of a self-complementary, HSE-containing, 28 base oligonucleotide having the sequence:

5'-GATCCTAGAAGCTTCTAGAAGCTT-CTAG-3'

Such a column is preferably prepared in accordance with the method of Kadonaga et al. (*Proc. Natl. Acad. Sci. USA* 83:5889 (1986), which reference is incorporated by reference). The oligonucleotide is preferably covalently attached to Sepharose CL-2B (Pharmacia) using cyanogen bromide to form the affinity column.

The pooled HSF-containing fractions are then applied to the above-described sequence specific double-stranded DNA affinity column. Activated HSF binds to the column, and can be eluted from the column in a 0.75M KCl salt wash. Fractions exhibiting HSF activity are then pooled in preparation for further purification.

The pooled fractions are then preferably diluted to 0.1M KCl and applied to a MONO Q FPLC column (Pharmacia). The bound material is preferably eluted with a linear gradient of KCl (0.1 to 1.0M). HSF activity is assayed, preferably in the manner described above, and active fractions are pooled. HSF activity is eluted from the column at 0.3–0.6M KCl.

Using the above-described procedure, activated HSF, capable of binding to DNA can be isolated and purified.

HSF and its Functional Derivatives, Agonists and Antagonists

The present invention pertains to activated heat shock factor ("HSF"), to therapeutic fragments of this factor, as well as to functional derivatives, agonists and antagonists of this factor. The invention especially concerns agents which are capable of activating HSF into is active form.

A "functional derivative" of HSF is a compound which possesses a biological activity (either functional or structural) that is substantially similar to a biological activity of HSF. The term "functional derivatives" is intended to include the "fragments," "variants," "analogues," or "chemical derivatives" of a molecule. A "fragment" of a molecule such as HSF, is meant to refer to any polypeptide subset of the molecule. A "variant" of a molecule such as HSF is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analogue" of a molecule such as HSF is meant to refer to a molecule substantially similar in function but not in structure to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

An "antagonist" of HSF is a compound which inhibits the function of HSF. Such antagonists can be immunoglobulins (such as, for example, monoclonal or polyclonal antibody, of active fragments of such antibody). The antagonists of the present invention may also include non-immunoglobulin compounds (such as polypeptides, organic compounds, etc.).

Polyclonal antibody capable of binding to activated HSF can be prepared by immunizing a mammal with a preparation of activated HSF or functional derivative of HSF. Methods for accomplishing such immunizations are well known in the art. Monoclonal antibodies (or fragments thereof) can also be employed to assay for the presence (or amount) of activated HSF in a particular biological sample. Such antibodies can be produced by immunizing splenocytes with activated HSF (by modifying the procedures of Kohler et al. (*Nature* 256:495 (1975); *Eur. J. Immunol.* 6:511 (1976); *Euro J. Immunol.* 6:292 (1976)).

In addition to the above methods, antibodies capable of binding to activated HSF may be produced in a two step procedure through the use of anti-idiotypic antibodies. Such a method makes use of the fact that antibodies are themselves antigens, and that, therefore, it is possible to obtain an antibody which binds to a second antibody. In accordance with this method, antibodies capable of binding to activated HSF are used to immunize an animal. The splenocytes of such an animal are then used to produce hybridoma cells, and the hybridoma cells are screened to identify clones which produce antibody whose ability to bind to anti-activated HSF antibodies can be specifically blocked by activated HSF protein. Such antibodies comprised anti-idiotypic antibodies to the anti-HSF antibody. Such antibodies can be used to immunize an animal, and thereby induce the formation of antibodies capable of binding to activated HSF.

In addition to providing additional HSF (or a functional derivative of HSF) to a subject, the efficacy of HSF in a subject can be increased by the administration of an agonist of HSF to a subject. The invention additionally pertains to such agonists of HSF. An agonist of HSF is any compound which is capable of increasing the efficacy of a function of HSF. Examples of such agonists include an agent which promotes the synthesis of HSF by the subject, an agent which promotes the activation of pre-existing HSF, etc. Agents which promote the activation of pre-existing HSF are the preferred agonists and therapeutic agents of the present invention.

HSF or agents which promote the activation of HSF may be obtained either synthetically, through the use of recombinant DNA technology, or by proteolysis. The therapeutic advantages of such agents may be augmented through the combined administration of several agents. The scope of the present invention is further intended to include functional derivatives of HSF which lack one, two, or more amino acid residues, or which contain altered amino acid residues, so long as such derivatives exhibit the capacity to influence the heat shock response.

The compounds of the present invention are said to be "substantially free of natural contaminants" if preparations which contain them are substantially free of materials with which these products are normally and naturally found.

Methods for Preparing HSF

The heat shock factor of the present invention may be obtained by natural processes (such as, for example, by inducing the production of HSF from a human or animal cell); by synthetic methods (such as, for example, by using the Merrifield method for synthesizing polypeptides to synthesize HSF, functional derivatives of HSF, or agonists or antagonists of HSF (either immunoglobulin or non-immunoglobulin)); or by the application of recombinant technology (such as, for example, to produce the HSF of the present invention in diverse hosts (i.e., yeast, bacteria, fungi, cultured mammalian cells, etc.), or from recombinant plasmids or viral vectors). The choice of which method to employ will depend upon factors such as convenience, desired yield, etc. It is not necessary to employ only one of the above-described methods, processes, or technologies to produce HSF; the above-described processes, methods, and technologies may be combined in order to obtain HSF. It is most preferable to prepare HSF by cloning and expressing a gene or cDNA sequence which encodes the preactivated HSF protein. Such gene cDNA sequence in hereinafter termed the "HSF gene" or "HSF cDNA sequence."

Any of a variety of procedures may be used to clone either the HSF gene (or, equivalently, a cDNA sequence which encodes HSF). One such method entails analyzing a shuttle vector library of cDNA inserts (derived from an HSF expressing cell) for the presence of an insert which contains the HSF gene or cDNA sequence. Such an analysis may be conducted by transfecting cells with the vector and then assaying for HSF expression.

The preferred method for cloning this gene entails determining the amino acid sequence of the HSF molecule. To accomplish this task, HSF protein may be purified, as described above, and analyzed by automated sequenators. Alternatively, the molecule may be fragmented as with cyanogen bromide, or with proteases such as papain, chymotrypsin or, preferably, trypsin (Oike, Y. et al., *J. Biol. Chem.* 257:9751–9758 (1982); Liu, C. et al., *Int. J. Pept. Protein Res.* 21:209–215 (1983)). Although it is possible to determine the entire amino acid sequence of HSF, it is preferable to determine the sequence of peptide fragments of the molecule. If the peptides are greater than 10 amino acids long, the sequence information is generally sufficient to permit one to clone a gene such as the gene for HSF (or a cDNA gene sequence of the HSF gene).

Once one or more suitable peptide fragments have been sequenced, the DNA sequences capable of encoding them are examined. Because the genetic code is degenerate, more than one codon may be used to encode a particular amino acid (Watson, J. D., *In: Molecular Biology of the Gene*. 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene sequence which encodes the peptide fragment, only one member of the set contains a nucleotide sequence that is identical to the nucleotide sequence of this gene sequence. Because this member is present within the set, and is capable of hybridizing to DNA even in the presence of the other members of the set, it is possible to employ the unfractionated set of oligonucleotides in the same manner in which one would employ a single oligonucleotide to clone the gene (or cDNA sequence) that encodes the peptide.

In a manner exactly analogous to that described above, one may employ an oligonucleotide (or set of oligonucleotides) which have a nucleotide sequence that is complementary to the oligonucleotide sequence or set of sequences that is capable of encoding the peptide fragment.

A suitable oligonucleotide, or set of oligonucleotides which is capable of encoding a fragment of the HSF gene (or which is complementary to such an oligonucleotide, or set of oligonucleotides) is identified (using the above-described procedure), synthesized, and hybridized, by means well known in the art, against a DNA or, more preferably, a cDNA preparation derived from human cells which are capable of expressing HSF gene sequences. Techniques of nucleic acid hybridization are disclosed by Maniatis, T. et al., *In: Molecular Cloning, a Laboratory Manual*, Cold Spring Harbor, N.Y. (1982), and by Haymes, B. D. et al., *In: Nucleic Acid Hybridization, a Practical Approach*. IRL Press, Washington, D.C. (1985), which references are herein incorporated by reference. The source of DNA or cDNA used will preferably have been enriched for HSF sequences. Such enrichment can most easily be obtained by using cDNA obtained by extracting RNA from cells cultured under conditions which induce HSF synthesis.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene (Walter, P. et al., *Proc. Natl. Acad. Sci. USA* 82:7889–7893 (1985)), tissue-type plasminogen activator (Pennica, D. et al., *Nature* 301:214–221 (1983)) and human term placental alkaline phosphatase complementary DNA (Kam, W. et al., *Proc. Natl. Acad. Sci. USA* 82:8715–8719 (1985)).

In a preferred alternative way of cloning an HSF gene sequence, a library of expression vectors is prepared by cloning DNA or, more preferably cDNA, from a cell capable of expressing HSF, into an expression vector. The library is then screened for members capable of expressing a protein which binds to anti-HSF antibody, and which has a nucleotide sequence that is capable of encoding polypeptides that have the same amino acid sequence as HSF or fragments of HSF.

The cloned HSF gene, obtained through the methods described above, may be operably linked to an expression vector, and introduced into bacterial, or eukaryotic cells to produce HSF protein. Techniques for such manipulations are disclosed by Maniatis, T. et al., supra, and are well known in the art.

Uses for HSF and its Functional Derivatives, Agonists and Antagonists

A. Diagnostic Uses

The compounds of the present invention may be used to diagnose the presence of stress in organs or tissue, or in extracts, sections, etc. of organs or tissues. The compounds of the present invention can also be used to diagnose the level of stress in cells or cellular extracts. The ability to perform such a diagnosis is especially desirable in evaluating the suitability of organs (such as, for example, kidney, liver, heart, etc.) or tissue (skin, bone marrow, etc.) in organ or tissue transplant or replacement therapies.

The presence, or level, of stress in a particular biological sample can be determined by identifying or quantifying the level of activated HSF which is present in that sample. Any of a variety of methods which are capable of identifying (or quantifying) the level of activated HSF in a sample can be used for this purpose. It is, however, most preferably to assay for activated HSF using an antibody, and especially a monoclonal antibody (or a fragment of either a polyclonal or a monoclonal antibody) which is capable of binding to activated HSF.

Diagnostic assays to detect activated HSF may comprise imaging assays (such as, for example, whole body or organ imaging) or may comprise a biopsy or in sito assay of cells or of organ or tissue sections. As indicated above, such assays may be conducted upon subcellular extracts from organs, tissues, cells, etc.

The antibodies (or fragments thereof) of the present invention are particularly suited for use in immunoassays wherein they may be utilized in liquid phase or bound to a solid-phase carrier.

Antibodies, or fragments thereof, may be labeled using any of a variety of labels and method of labeling. Examples of types of labels which can be used in the present invention include, but are not limited to, enzyme labels, radioisotopic labels, non-radioactive isotopic labels, fluorescent labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, etc. $^{111}$In is a preferred isotope. Its use may have substantial advantages since its avoids the problem of dehalogenation of the $^{125}$I or $^{131}$I-labeled monoclonal antibody by the liver. In addition, this radionucleotide has a more favorable gamma emission energy for imaging (Perkins, A. C., et al., *Eur. J. Nucl. Med.* 10:296-201 (1985); Carasquillo, J. A., et al., *J. Nucl. Med.* 28:281-287 (1987)).

Examples of suitable non-radioactive isotopic labels include $^{157}$Gd, $^{55}$Mn, $^{162}$Dy, $^{52}$Tr, $^{56}$Fe, etc.

Examples of suitable fluorescent labels include a $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinal skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1-31 (1976)), and Schurs, A. H. W. M., et al. (*Clin. Chim. Acta* 81:1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to HSF. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The antibodies, or fragments of antibodies, of the present invention may be used to quantitatively or qualitatively detect the presence of activated HSF. Such detection may be accomplished using any of a variety of immunoassays. For example, by radioactively labeling the antibodies or antibody fragments, it is possible to detect activated HSF through the use of radioimmune assays. Activated HSF can be distinguished from "preactivated" HSF by its capacity to bind to HSE-containing DNA. The amount of such activated HSF present in a sample can be measured using a radioimmune assay. A good description of a radioimmune assay (RIA) may be found in *Laboratory Techniques and Biochemistry in Molecular Biology*. by Work, T. S., et al., North Holland Publishing Company, NY (1978), with particular reference to the chapter entitled "An Introduction to Radioimmune Assay and Related Techniques" by Chard, T., incorporated by reference herein.

The antibody or antibody fragments of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, cellular extract etc.) and a quantity of detectably labeled soluble antibody is added to permit detection and/or quantitation of the ternary complex formed between solid-phase antibody, activated HSF, and labeled antibody.

Typical immunometric assays include "forward" assays in which the antibody bound to the solid phase is first contacted with the sample being tested to extract the activated HSF from the sample by formation of a binary solid phase antibody-HSF complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the activated HSF bound to the solid support through the unlabeled antibody, the solid support is washed a second time to remove the unreacted labeled antibody. This type of forward sandwich assay may be a simple "yes/no" assay to determine whether activated HSF is present or may be made quantitative by comparing the measure of labeled antibody with that obtained for a standard sample containing known quantities of HSF. Such "two-site" or "sandwich" assays are described by Wide at pages 199-206 of *Radioimmune Assay Method,* edited by Kirkham and Hunter, E. & S. Livingstone, Edinburgh, 1970.

In another type of "sandwich" assay, which may also be useful to assay the activated HSF of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplex labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

As explained above, the immunometric assays for HSF require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

B. Use of the Compounds of the Present Invention To Detect Agents Which Activate HSF As discussed above, the presence of activated HSF in a cell permits the cell to survive heat shock and other stressful conditions. Hence, an agent which is capable of activating HSF, or which is capable of stimulating or enhancing the natural activation of HSF would be extremely desirable. Such an agent could be used to prevent cell death (i.e. to prevent the death of organs, tissue, etc., while it is being prepared for transplant into a recipient) or to treat an individual in stress whose own natural capacity for activating HSF is insufficient to prevent injury or death.

Agents which activate HSF can be identified in the following manner. HSF is incubated in the presence of a suitable amount of an agent whose capacity to activate HSF is to be determined. The incubation mixture contains the enzymes, co-enzymes, co-factors, etc. which are required in order to permit activation of HSF to occur. Preferably, such incubation mixtures are composed of cellular extracts of mammalian cells. After incubation for a suitable period of time, the HSF in the incubation mixture is tested for its capacity to bind to DNA. Since HSF binds to DNA only when activated, the presence of DNA-bound HSF (or, alternatively, an increase in the amount of DNA-bound HSF) indicates that the assayed agent was capable of activating the HSF of incubation mixture. Once such an agent has been identified, its structure can be determined through routine chemical or biochemical analysis. The above-described assay for such activating agents is especially amenable for use in screening large numbers of potential pharmacological agents.

C. Therapeutic Uses

Agents which increase the level of activated HSF in a subject (i.e. a human or an animal) may be used in the therapy of any disease associated with the heat shock stress response. As discussed above, the heat shock response is a very highly evolutionarily conserved pathway that an organism uses to respond to a variety of stresses. Included in these stresses are hypoxia and ethanol.

The pathophysiologic manifestations of hypoxia are well documented. Hypoxia is the mechanism that is directly responsible for both myocardial and cerebral infarctions. Hence, if a human or animal were better able to respond to an hypoxic insult, it would potentially survive the insult with less permanent damage. The limitation of myocardial infarct size has been shown to directly affect patient survival. Agents which increase the level of activated HSF in a subject thus have utility in potentiating such stress. Such therapy is also valuable in the treatment of ethanol induced stress, due to its capacity to limit the metabolic derangement that results from an overdose of ethanol.

In providing a patient with antibodies, or fragments thereof, capable of binding to HSF, or when providing HSF (or a fragment, variant, or derivatives thereof) or an agent capable of promoting the activation of HSF to a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing the above-described compounds to a patient, it is preferable to administer such compounds in a dosage which also ranges from about 1 pg/kg to 10 mg/kg (body weight of patient) although a lower or higher dosage may also be administered.

The compounds of the present invention may be administered to patients intravenously, intramuscularly, subcutaneously, enterally, or parenterally. When administering such compounds by injection, the administration may be by continuous infusion, or by single or multiple boluses.

The compounds of the present invention are intended to be provided to recipient subjects in an amount sufficient to effect the heat shock response. An amount is said to be sufficient to "effect" the heat shock response if the dosage, route of administration, etc. of the agent are sufficient to influence such a response.

The compounds of the present invention may be provided either prior to the onset of a stress-causing condition (so as to suppress the anticipated damage of such a condition) or after the initiation of the condition.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Assay for Heat Shock Factor

Human HSF bound to the HSE can be detected as a complex that migrates with a characteristic mobjlity on a non-denaturing polyacrylamide gel (Kingston R. E. et al., *Mol. Cell. Biol.* 7:1530 (1987); Sorger, P. K. et al., *Nature* 329:81 (1987), which references are hereby incorporated by reference). FIG. 1 shows the mobility of human HSF on a non-denaturing polyacrylamide gel. Nuclear extracts were prepared from 1 liter of HeLa cells by the method of Dignam et al. (*Nucl. Acids Res.* 11:1475 (1983)) immediately after 1 h of incubation at 43° C. extract, lanes 1 to 3 and 8 to 10) or from cells growing normally at 37° C. (37° C. extract, lanes 4 to 6 and 11 to 13). The indicated amounts of extract (lanes 1, 4, 8, and 10 $\mu$g of protein; lanes 2, 5, 9, and 12 3.3 $\mu$g of protein; lanes 3, 6, 10, and 13 1 $\mu$g of protein; and lanes 7 and 14, 0 $\mu$g of protein) were incubated with an end-labeled DNA fragment for 30 min at 30° C. and subjected to electrophoresis on a 4% nondenaturing polyacrylamide gel. The labeled fragment contained bases $-148$ to $-74$ (lanes 1 to 7) or bases $-188$ to $-74$ (lanes 8 to 14) of the human hsp70 promoter. Binding reaction mixtures (20 $\mu$l) contained 12 mM N-2-hydroxyethyl-piperazine-N'-2-ethanesulfonic acid (HEPES) (pH 7.9), 12% (vol/vol) glycerol, 60 mM KCl, 0.12 mM EDTA, 0.3 mM phenylmethylsulfonyl fluoride, 0.3 mM dithiothreitol, 2 mM MgCl$_2$, 100 $\mu$g of poly(dI-dC)·poly(dI-dC) per ml, approximately 0.2 ng of the indicated labeled DNA, and the indicated amount of extract protein. H, Heat-induced factor; C, CAAT-binding factor; FREE, unbound DNA; HS BOX, location of the heat shock element; CAT, location of the sequence CCAATC. Nuclear extracts from HeLa cells growing at 43° C. contain significantly more of this binding activity than do nuclear extracts from HeLa cells growing at 37° C. In order to develop an in vitro system to study this induction, nuclear and cytoplasmic extracts were prepared from HeLa cells growing at 37° C. (Dignam, D. et al., *Nucl. Acids Res* 11:1475 (1983), which reference is hereby incorporated by reference herein). These extracts were heated at 43° C. for one hour and the level of HSE binding activity was determined using the band retention technique.

Nuclear and Cytoplasmic extracts were prepared according to Digman et al. (*Nucl Acids Res.* 11:1475 (1983)). Buffers used for extract preparation are designated as follows: buffer A contains 10 mM HEPES (pH 7.9 at 4° C.), 1.5 mM MgCl$_2$, 10 mM KCl and 0.5 mM DTT; buffer B contains 0.3M HEPES (pH 7.9), 1.4M KCl and 0.03M MgCl$_2$; buffer C contains 20 mM HEPES (pH 7.9), 25% (v/v) glycerol, 0.42M NaCl, 1.5 mM MgCl$_2$, 0.2 mM EDTA, 0.5 mM phenylmethylsulfonyl fluoride (PMSF) and 0.5 mM DTT; buffer D contains 20 mM HEPES (pH 7.9), 20% (v/v) glycerol, 0.1M KCl, 0.2 mM EDTA, 0.5 mM PMSF, and 0.5 mM DTT. DTT and PMSF were added fresh to the buffers just before use.

Standard Procedure for Extract Preparation

HeLa cells were harvested from cell culture media by centrifugation (at room temperature) for 10 min at 200 rpm in a Sorvall HG4 rotor. Pelleted cells were then suspended in five volumes of 4° C. phosphate buffered saline and collected by centrifugation as detailed above; subsequent steps were performed at 4° C. The cells were suspended in five packed cell pellet volumes of buffer A and allowed to stand for 10 min. The cells were called by centrifugation as before and suspended in two packed cell pellet volumes (volume prior to the initial wash with buffer A) of buffer A and lysed by 190 strokes of a Kontes all-glass Dounce homogenizer (B type pestle). The homogenate was checked microscopically for cell lysis and centrifuged for 10 min at 2000 rpm in a Sorvall HG4L rotor to pellet nuclei. The supernatant was carefully decanted, mixed with 0.11 volumes of buffer B, and centrifuged for 60 min at 100,000 g$_{av}$ (Beckman Type 42 rotor). The high-speed supernatant from this step was dialyzed five to eight hours against 20 volumes of buffer D and is designated the S100 fraction.

The nuclear extract was prepared as follows. The pellet obtained from the low-speed centrifugation of the homogenate was subjected to a second centrifugation for 20 min at 25,000 $g_{av}$ (Sorvall SS34 rotor), to remove residual cytoplasmic material and this pellet was designated as crude nuclei. These crude nuclei were resuspended in 3 ml of buffer C per $10^9$ cells with a Kontes all-glass Dounce homogenizer (10 strokes with a type B pestle). The resulting suspension was stirred gently with a magnetic stirring bar for 30 min and then centrifuged for 30 min at 25,000 $g_{av}$ (Sorval SS34 rotor). The resulting clear supernatant was dialyzed against 50 volumes of buffer D for five hours. The dialysate was centrifuged at 25,000 $g_{av}$ (Sorvall SS34 rotor) for 20 min and the resulting precipitate discarded. The supernatant, designated the nuclear extract, was frozen as aliquots in liquid nitrogen and stored at $-80°$. The protein concentration was usually 6 to 8 mg per ml and 15 to 20 mg of protein were obtained from $10^9$ cells.

Nuclear and cytoplasmic extracts from 4 L of HeLa cells growing at 37° C. (denoted NE and S100, respectively), and nuclear extracts from 1 L of HeLa cells immediately after a 1 hr incubation at 43° C. (HSNE) were prepared as described by Dignam et al. (*Nucl. Acids Res* 11:1475 (1983)). Extracts were dialyzed into buffer (20 mM Hepes, pH 7.9, 20% (vol/vol) glycerol, 100 mM KCl, 0.2 mM EDTA, 0.5 mM phenylmethylsulfonyl fluoride, 0.5 mM dithiothreitol) and were incubated without any addition. Protein (5.0 μg of protein of the NE or 8.5 μg S100, or both) were incubated for 1 hr at either 0° C. or 43° C. The extracts were then incubated at 30° C. for 30 min with a $^{32}P$. labeled synthetic oligonucleotide containing the HSE (bases $-11$ to $-80$) of the human hsp70 promoter (Sen, R. et al.; *Cell* 47:921 (1986); Prywes, R. et al., *Cell* 47:777 (1986); Hayes, T. E. et al., *Proc. Natl. Acad. Sci. USA* 84:1272 (1987)). Binding reaction mixtures (20 μl) contained 12 mM HEPES, pH 7.9, 12% (vol/vol) glycerol, 60 mM KCl, 0.12 mM EDTA, 0.3 mM phenylmethylsulfonyl fluoride, 0.3 mM dithiothreitol, 2 mM $MgCl_2$, 100 μg of poly(dI-dC).poly(dI-dC) per mol, approximately 0.2 ng of the labeled DNA, and extract. The reaction mixtures were then subjected to electrophoresis on a 4% non-denaturing polyacrylamide gel.

A 36-mer double-stranded oligonucleotide containing the HSE (bases $-80$ to $-115$ of a human hsp70 promoter) was used as labelled probe. The nuclear extract contained no binding activity either before or after heating, while the cytoplasmic extract was found to have significant levels of binding activity only after incubation at 43° C. Addition of nuclear extract to cytoplasmic extract did not alter the extent of induction.

The results of this experiment show that cytoplasmic extracts from non-heat induced HeLa cells contain a heat inducible activity binding in the region of the heat shock element determined by a gel mobility shift assay.

EXAMPLE 2

Purification of the Heat Shock Factor

A) Preparation of Nuclear Extract

Human HeLa cells were grown in suspension culture supported by Minimal Essential Media (Joklik's Modification) which was supplemented with 5% Horse serum. Cells were grown to a density of approximately 500,000 cells per milliliter. Cells were then harvested and nuclear extracts were prepared essentially as described by Dignam et al. (*Nucl. Acids Res* 11:1475 (1983). The nuclear extract was dialyzed into Dignam Buffer D (20% v/v glycerol, 20 mM HEPES (pH 7.9), 0.1M KCl, 0.5 mM DTT, 0.5 mM PMSF, 0.2 mM EDTA).

B) Fractionation Step #1

The HeLa cell nuclear extract in Dignam Buffer D was passed over a Calf Thymus Double Stranded DNA-Cellulose Column (Pharmacia) which had been pre-equilibrated in Buffer D. The column was eluted with step increments of Buffer D containing 0.3M KCl and 1.5M KCl. The HSF activity was monitored with the gel electrophoresis mobility shift assay of Kingston et al. (*Mol. Cell. Biol.* 7:1530 (1987)). The HSF activity was found to elute at 0.3M KCl. Fractions containing HSF activity were pooled and the detergent NP-40 was added to 0.1% (v/v).

C) Fractionation Step #2

The second purification step relied on the specific binding of HSF to its cognate sequence—the HSE. For this step, a sequence-specific double-stranded oligonucleotide affinity column was constructed according to the method of Kadonaga et al. (*Proc. Natl. Acad. Sci. USA* 83:5889 (1986)). A self-complimentary 28 base oligonucleotide was synthesized with the following sequence:

5'-GATCCTAGAAGCTTCTAGAAGCTT-CTAG-3'

This oligonucleotide was self-annealed to form a double-stranded molecule with GATC 5' overhangs and two overlapping HSEs. These molecules were phosphorylated and ligated into concatamers with an average length of about 5 to 10 units. This DNA was covalently attached to Sepharose CL-2B (Pharmacia) using cyanogen bromide. This, then, constituted the affinity column.

Pooled fractions from Step #1 were applied to the affinity column which had been pre-equilibrated in Buffer 0.3D'ins (Buffer D with 0.3M KCl, 0.1% v/v NP-40, and 0.1 mg/ml bovine insulin). The HSF activity was eluted with one step wash of Buffer 0.8D'ins (0.8M KCl, 0.1% v/v NP-40, and 0.1 mg/ml bovine insulin).

D) Fractionation Step #3

Pooled fractions from the previous step were diluted to 0.1M KCl and were applied to MONO Q FPLC column (Pharmacia). The column was eluted with a linear gradient of KCl from 0.1 to 1.0M fractions KCL in Buffer D'ins. HSF activity was assayed and active fractions were pooled. The eluted material produced 2 bands when analyzed by SDS gel electrophoresis. One of these bands is thought to be a degradation product of the other. Thus, the material is between 50 % pure (if the two bands are unrelated) and 95 % pure (if the two bands are related).

EXAMPLE 3

Characterization of the Heat Shock Factor

The cytoplasmic heat-inducible binding activity formed a single retained band that comigrated with the lower of two retained bands obtained with nuclear extract from heat shocked cells. Fractionation of the cytoplasmic extract on either phosphocellulose or Biorex 70 yields a fraction that produces two bands of appropriate mobility after incubation at 43° C. The presence of only the lower band after induction of the unfractionated extract at 43° C. may therefore be due to an inhibitor in the extract. The sequence specificity of this binding was examined in order to verify that the binding represented an interaction with the HSE.

The sequence specificity of the heat-inducible binding activity present in the S100 extract was characterized by examining the competition of the heat-induced band with fragments containing the heat shock element and nonspecific fragments. Competition of the heat-induced band with fragments containing the heat shock element and nonspecific fragments was investigated as follows. 8.5 μg of the S100 protein was incubated (or not incubated) at 43° C. for 1 hr prior to incubation with the DNA probe. S100 extracts were prepared and DNA incubations and electrophoresis were performed as described above. Incubation mixtures also contained either nonradioactive competitor DNA (bases −84 to +5 of the human hsp70 gene (which does not contain the heat shock element) in a 5- or 10-fold molar excess or bases −148 to −74 of the human hsp70 gene (which contains the heat shock element centered at base −100) or a 310-base-pair fragment of a *D. melanogaster* heat shock gene containing three heat shock elements (XhoI [base −200] to EcoRI [base +110], of plasmid pSP6-HS-9 (Wurm, F. M. et al., *Proc. Natl. Acad. Sci. USA* 83:5415 (1986)), derived from cloned fragment 232 described by Holmgren et al. (*Cell* 18:1359 (1979) or a 39-base-pair double-stranded synthetic oligonucleotide containing the CAAT sequence (top strand, 5'-CA CCG TCG ATT TCC CTT CTG AGC CAA TCA CCG AGC TCG A); or the 36-base-pair double-stranded synthetic oligonucleotide probe. DNA concentrations were estimated by agarose gel electrophoresis.

To further characterize the binding specificity, a methylation interference analysis was performed (Siebenlist, U. et al., *Proc. Natl. Acad. Sci. USA* 77:122 (9180); Gilman, M. Z. et al., *Mol. Cell. Biol* 6:4305 (1986)). A partially methylated fragment containing the HSE was incubated with heated cytoplasmic extract, and bound and free fragments were separated and analyzed. The analysis was performed with radioactive label on either the top or bottom strand. Cytoplasmic extract was heated at 43° C. for 1.5 hr. Binding reactions were performed as described above In such assays, 120 μg of heated cytoplasmic extract (IN VITRO) or 16 μg HSNE (IN VIVO) were incubated with 20 ng of a labeled fragment containing bases −148 to −74 of the promoter. Bound and free complexes were separated on a nondenaturing gel, eluted, and analyzed as described by Gilman, M. Z. et al. (*Mol. Cell. Biol.* 6:4305 (1986)). The heat shock consensus sequence is C—GAA—TT-C—G. All fragments that contained an HSE competed for binding, while there was no competition by fragments that did not contain the HSE. Five G residues in or adjacent to the HSE were underrepresented in bound DNA, indicating that the bound factor is in close contact with these residues. A similar pattern is seen with the factor found in nuclear extracts from heat-shocked HeLa cells. The competition data and this DMS interference data show that the binding activity induced in vitro has the same sequence specificity as that seen after induction in whole cells (Kingston R. E. et al., *Mol. Cell. Biol.* 7:1530 (1987)).

EXAMPLE 4

Characterization of the Induction of Binding

The induction of binding activity in intact HeLa cells was compared with the induction of HSE in a cell-free system. The induction of binding activity in intact HeLa cells was found to occur with rapid kinetics, whereas induction in the cell-free system occurs more slowly. Determinations of the kinetics and temperature dependence of the heat-inducible binding activity present in the S100 extract were performed as follows. S100 extracts were prepared and DNA incubation and electrophoresis were performed as described in the above. Samples contained 8.5 μg of protein from the S100 extract. Samples were incubated for 1 hr. at 43° C. prior to performing the binding reactions. After this incubation, some samples were then incubated for 1 additional hr. at 37° C., 30° C., or 0° C. prior to binding reactions. S100 extracts were incubated at 43° C. prior to binding reactions. Peak levels of binding activity were seen after 45 to 60 minutes of incubation at 43° C. The optimal temperature for induction of binding activity closely correlated with the temperature at which HeLa cells undergo the heat shock response. There was a very slight induction of the binding ability at 37° C. in vitro, with increased induction seen at 40° C. and 43° C. and no induction was seen at 50° C. Once binding ability was induced, it was found to be stable; after induction at 43° C., further incubation on ice, at 30° C. or at 37° C. for up to one hour did not result in deactivation of the activated factor.

EXAMPLE 5

Induction of HSF from Hela Cells

The amount of HSF in a cytoplasmic extract that had been heated for one hour at 43° C. was determined by using the mobility shift gel under conditions where the amount of measured HSF increased linearly with increasing protein. The amount of HSF in a nuclear extract from HeLA cells heated intact at 43° C. was measured in the same manner. The activities were then corrected for the number of cells that had been used to produce the respective extracts. The amount of HSF in the heated cytoplasmic extract was 12,200 units per $10^6$ cells, while the nuclear extract from heated cells contained 11,800 units per $10^6$ cells. Units are defined by the amount of labelled HSE probe retained on a mobility shift gel.

The characteristics of the in vitro induction of binding ability of HSF strongly suggest that this activation mirrors that seen when intact HeLa cells are heat-shocked. HSE-binding specificity after in vitro activation is identical to that seen when factor is isolated from heat-shocked HeLa cells. The temperature profile for induction in vitro is similar to that seen in intact cells. Additionally, activation of HSe-binding activity in vitro is efficient. Induction of a cytoplasmic extract in vitro results in 12.2 units of HSF per $10^6$ cells, while nuclei of heat-shocked HeLa cells contain 11.8 units of HSF per $10^6$ cells.

EXAMPLE 6

Effect of Temperature on HSF Activation

Heated cells contain increased levels of denatured protein, and it has been suggested that this triggers activation of HSF via a protein degradation pathway (Anantham, J. et al., *Science* 232:522 (1986); Finley, D. et al., *Cell* 17:43 (1984); Goff, S. A. et al., *Cell* 41:587 (1985); Munro, S. et al., *Nature* (London) 317:477 (1985)). This model predicts that activation occurs in a temperature dependent fashion in the in vitro system because there is more denatured protein at 43° C. than at 37° C. In contrast, addition of boiled BSA to the cytoplasmic extract did not change the rate of induction of HSF at either 37° C. or 43° C. (see above) nor did it change the extent of induction. Addition of boiled cytoplasmic extract also had very little effect on activation. Thus, denatured protein does not play a role in changing HSF to a form that can bind DNA, suggesting that this alteration may result from a direct effect of temperature.

EXAMPLE 7

Molecular Mechanism of HSF Activation

Fractionation of the cytoplasmic extract on several ion-exchange columns results in individual fractions that retain the ability to activate HSF in a heat-inducible manner. These fractions were used to show that addition of ATP has no effect on the rate or extent of activation of binding activity. A cytoplasmic extract was applied to a Biorex 70 column an diluted with washes containing 0.1, 0.2, 0.5 and 1.0M KCl. Fractions were assayed individually and in combination for the ability to form active HSF upon incubation at 43° C. All of this activity eluted in the 0.1M KCl wash. One of the protein factors retained on this column ("X") was found to have a faster mobility than HSF. The activity that form X eluted in the 0.5M KCl wash. The 0.5M wash had no ability to form active HSF, and did not alter the amount of HSF formed when added to the 0.1M KCl wash. This finding is consistent with a model where an individual, inactive HSF molecule undergoes a heat-induced conformation change to a DNA-binding form. However, the extent of activation of HSF is exquisitely sensitive to dilution of the cytoplasmic extract, indicating that at least two molecules are needed to activate HSF. These results indicate either that (1) inactive HSF exists as a monomer which undergoes a conformational change and dimerization to form an active species capable of binding, or (2) a second, heat-sensitive factor exists which modifies HSF to a DNA-binding form.

As indicated above, the assay of HSF activation revealed the presence of a band ("X") whose level was inversely correlated with the amount of HSF. This finding suggests that this band represents a precursor of active HSF. However, the activity that forms this band separates from the activity that forms active HSF on negatively charged columns. Thus, it is unlikely that the factor that produces X is a precursor to active HSF, although a role for X in regulation of the heat shock response remains possible.

EXAMPLE 8

Crosslinking Studies

The characteristics of activation of HSF in vitro were investigated by assessing the level of HSF present after the following manipulations as determined by the above described gel mobility shift assay using a synthetic oligonucleotide containing an HSE (see above).

A) 20 µg of S100 protein was incubated for 20 min in the presence or absence of boiled bovine serum albumin (10 µg BSA protein/20 µg S100 protein). This experiment revealed that the addition of denatured protein does not alter activation.

B) Cytoplasmic extract was diluted with an equal volume, 4 vol or 9 vol of boiled cytoplasmic extract prior to incubation for 90 min. Activity was then assayed in binding reactions (20 µl) that all contained 13 µg of active (nonboiled) cytoplasmic extract. This experiment revealed that dilution reduced activation of HSF in vitro. Similar results were obtained after dilution with buffer.

C) Cytoplasmic extract (13 mg/ml) was either heated for 1 hr. at 43° C. ("43° C. extract") or incubated on ice for 1 hr. ("0° C. extract"). The 43° C. extract (either 1 µl, 3 µl, or 0 µl) was incubated with an amount of 0° C. extract (either 0 µl, 2 µl or 4 µl) at 30° C. for 1 hr. This experiment revealed that addition of non-heated extract did not inhibit binding to the HSE.

The HSF band had the following characteristics: it is not present in control nuclear extracts; it is present in the HSF-HSE complex identified on mobility shift gels; and its formation is efficiently competed by an oligonucleotide that contains an HSE, but not by a control oligonucleotide specifying the CCAAT element.

UV crosslinking studies were performed in order to determine the apparent size of each factor. Extracts were incubated with a synthetic, dimerized HSE that had been substituted with $\alpha$ $^{32}$P-CTP and bromo-deoxyuridine, and the resultant HSF containing complex was separated from non-specific complexes on an agarose gel and irradiated with UV light. Analysis of the resultant labelled protein species on an SDS polyacrylamide gel revealed a band migrating at 93 kd that was present in nuclear extracts from heated HeLa cells.

Surprisingly, similar experiments with the heated cytoplasmic extract revealed that HSF activated in vitro runs markedly faster (90 kd) on a polyacrylamide gel than HSF isolated from nuclei of heated cells. It is not present in cytoplasmic extract that has not been heated, and formation of the crosslinked complex is competed by an HSE but not by a control CCAAT oligonucleotide. Thus, HSF activated for DNA-binding specificity in vitro differs in some way from HSF isolated from heat shocked cells. This difference is not caused by an activity in cytoplasmic extracts that modifies active HSF, as both the 93 kd and 90 kd form of HSF are observed after heating a cytoplasmic extract in the presence of nuclear extract.

One possibility for this difference in mobility, by analogy with Yeast HSF, is phosphorylation. Yeast HSF increases in apparent molecular weight upon heat shock of yeast cells, and this change appears to be caused by phosphorylation. HSF from heated HeLa cells and in vitro activated HSF were treated with acid phosphatase prior to crosslinking the factor to DNA. Treatment with acid phosphatase increased the apparent mobility of HSF that had been isolated from heated HeLa cells, while treatment with calf intestinal phosphatase had a limited effect. Treatment of HSF from heated cells with both phosphatases resulted in a diffuse band that extended from approximately 90 kd to 92 kd. In contrast, there was no detectable effect of acid phosphatase on the mobility of the in vitro activated HSF. Although phosphatase treatment did not change the mobility of HSF from heated cells to precisely that of in vitro activated HSF, these results imply that HSF found in intact heated cells is more extensively phosphorylated than HSF that has been activated in vitro.

The HSE-binding capabilities of human HSF can, thus, be activated by heating a HeLa cytoplasmic extract. Denatured protein does not alter the rate or extent of activation of the HSE binding activity in vitro. HSF that has been activated in vitro has DNA-binding capabilities that are identical to HSF isolated from the nuclei of heated human cells, however the in vitro activated HSF runs with faster mobility on polyacrylamide gels than does HSF activated in intact cells. This difference in mobility appears to be due to differences in phosphorylation. Thus, human cells respond to heat by activating HSF by at least two steps: first, an ATP-independent heat-induced alteration in DNA-binding capability, followed by phosphorylation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of diagnosing a stress condition of a patient comprising:
   a. contacting a sample obtained from said patient with a compound that specifically binds to activated heat shock factor;
   b. determining the amount of bound compound as a measure of the level of said activated heat shock factor in said sample; and
   c. using said determination to correlate the level of said heat shock factor with the presence of a stress condition of a patient, wherein said stress condition is selected from the group consisting of a myocardial infarction, cerebral infarction, a hypoxic insult and an ethanol-induced metabolic stress.

2. The method of claim 1, wherein said compound is an antibody or fragment thereof.

3. The method of claim 2, wherein said antibody is a monoclonal antibody.

4. The method of claim 2, wherein said antibody is a polyclonal antibody.

5. The method of claim 1, wherein said sample is selected from the group consisting of an organ, a tissue, and a cell.

6. The method of claim 1, wherein said sample is an organ, a tissue or a cellular extract.

7. The method of claim 1, wherein said compound is detectably labeled.

8. A method of diagnosing a stress condition in a patient comprising:
   a. administering to said patient an effective amount of a compound that specifically binds to activated heat shock factor;
   b. determining the amount of bound compound as a measure of the level of said activated heat shock factor in said patient using an imaging assay; and
   c. using said determination to correlate the level of said heat shock factor with the presence of a stress condition of a patient, wherein said stress condition is selected from the group consisting of a myocardial infarction, cerebral infarction, a hypoxic insult, and an ethanol-induced metabolic stress.

9. The method of claim 8, wherein said compound is an antibody or fragment thereof.

10. The method of claim 9, wherein said antibody is a monoclonal antibody.

11. The method of claim 9, wherein said antibody is a polyclonal antibody.

12. The method of claim 8, wherein said compound is detectably labeled.

13. The method of claim 1, wherein said compound is an oligonucleotide.

14. The method of claim 8, wherein said compound is an oligonucleotide.

* * * * *